(12) United States Patent
Abe

(10) Patent No.: US 7,168,806 B2
(45) Date of Patent: Jan. 30, 2007

(54) LASER TREATMENT APPARATUS

(75) Inventor: Hitoshi Abe, Okazaki (JP)

(73) Assignee: Nidek Co., Ltd., Aichi (JP)

( * ) Notice: Subject to any disclaimer, the term of this patent is extended or adjusted under 35 U.S.C. 154(b) by 158 days.

(21) Appl. No.: 10/959,988

(22) Filed: Oct. 8, 2004

(65) Prior Publication Data
US 2005/0080467 A1    Apr. 14, 2005

(30) Foreign Application Priority Data
Oct. 14, 2003  (JP) .............................. 2003-354378

(51) Int. Cl.
A61B 3/10   (2006.01)
A61B 18/18  (2006.01)

(52) U.S. Cl. ...................... 351/221; 351/205; 351/211; 606/4

(58) Field of Classification Search ................ 351/205, 351/207, 211, 218, 220, 221; 606/4–13, 606/16–1; 600/101, 104, 108
See application file for complete search history.

(56) References Cited
U.S. PATENT DOCUMENTS 4,477,159 A * 10/1984 Mizuno et al. ............. 351/221
4,580,559 A *  4/1986 L'Esperance ................ 606/3
5,252,999 A * 10/1993 Sukigara et al. ............ 361/221
5,400,092 A *  3/1995 Schepens et al. ........... 351/214
5,543,866 A *  8/1996 Van de Velde .............. 351/221
5,817,088 A * 10/1998 Sterling ....................... 606/4
5,923,399 A *  7/1999 Van de Velde .............. 351/221
6,089,716 A *  7/2000 Lashkari et al. ............ 352/221
6,350,031 B1 *  2/2002 Lashkari et al. ............ 351/221
6,537,269 B1 *  3/2003 Abe ............................ 606/12
6,758,564 B2 *  7/2004 Ferguson ..................... 351/221
6,830,335 B2 * 12/2004 Gutridge et al. ............. 351/221
2003/0009156 A1 *  1/2003 Levine ........................ 606/5
2005/0237486 A1 * 10/2005 Su et al. ...................... 351/206

FOREIGN PATENT DOCUMENTS

JP    A 57-078852    5/1982

* cited by examiner

Primary Examiner—A. Farah
(74) Attorney, Agent, or Firm—Oliff & Berridge, PLC

(57) ABSTRACT

A laser treatment apparatus comprises: a binocular indirect ophthalmoscope which is fixedly mounted on a head of an operator during use; an irradiation optical system which is placed in the ophthalmoscope and adapted to irradiate a treatment laser beam delivered into the ophthalmoscope to a treatment part of a patient; and a shift unit which is placed in the irradiation optical system and adapted to shift an irradiation position of the treatment beam in two-dimensional, vertical and horizontal directions.

3 Claims, 4 Drawing Sheets

LASER TREATMENT APPARATUS

BACKGROUND OF THE INVENTION

1. Field of the Invention

The present invention relates to a laser treatment apparatus for treating a part to be treated by irradiating a treatment laser beam to the part through the use of a binocular indirect ophthalmoscope.

2. Description of Related Art

There is a laser treatment apparatus for performing photocoagulation or other treatments by irradiating a part to be treated (hereinafter, a treatment part) with a treatment laser beam (hereinafter, a treatment beam) through the use of a binocular indirect ophthalmoscope which is fixedly mounted on the head of an operator during use (see Japanese unexamined patent publication No. 57(1982)-78852 and U.S. Pat. No. 5,252,999).

When using the conventional laser treatment apparatus using the binocular indirect ophthalmoscope, the operator has to align the treatment beam with the treatment part by moving his/her head vertically and horizontally. Accordingly, much skill is required to use such an apparatus and it likely imposes a burden on the operator.

SUMMARY OF THE INVENTION

The present invention has been made in view of the above circumstances and has an object to overcome the above problems and to provide a laser treatment apparatus which allows easy alignment of a treatment laser beam with a treatment part.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus comprising: a binocular indirect ophthalmoscope which is fixedly mounted on a head of an operator during use; an irradiation optical system which is placed in the ophthalmoscope and adapted to irradiate a treatment laser beam delivered into the ophthalmoscope to a treatment part of a patient; and a shift unit which is placed in the irradiation optical system and adapted to shift an irradiation position of the treatment beam in two-dimensional, vertical and horizontal directions.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
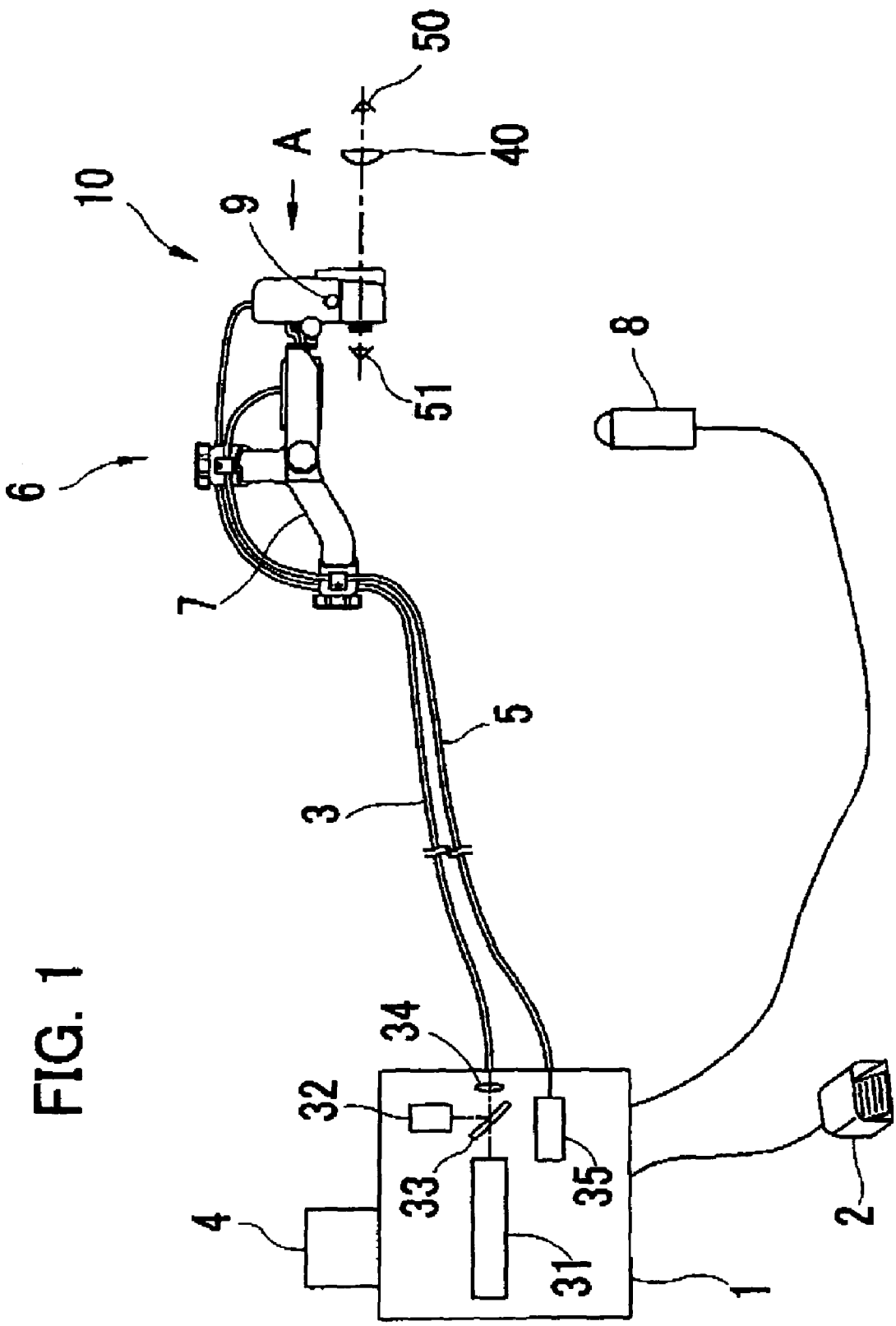
FIG. 1 is a schematic structural view of a laser treatment apparatus in a present embodiment.

A detailed description of a preferred embodiment of the present invention will now be given referring to the accompanying drawings. FIG. 1 is a schematic structural view of a laser treatment apparatus in the present embodiment. A laser oscillator 1 of the apparatus contains a treatment laser source 31 and an aiming laser source 32. The treatment laser source 31 includes an Nd:YAG crystal which is a solid-state laser medium, a semiconductor laser (a laser diode) used as an excitation source, and a nonlinear crystal used as a wavelength converter (a wavelength converting element). Light beams having oscillation lines (peak wavelengths) in a near-infrared region are emitted from the Nd:YAG crystal by excitation light, and among them, the second harmonic of the light beam having an oscillation line of about 1064 nm is generated through the nonlinear crystal, A treatment laser beam having a wavelength of about 532 nm (green) is thus emitted. The aiming laser source 32 is a semiconductor laser (a laser diode) which emits an aiming laser beam having a wavelength of about 630 nm (red).

In the oscillator 1, the treatment beam and the aiming beam are made to coincide with each other by a dichroic mirror 33 and then enter an optical fiber cable 3 through a condensing lens 34. The optical fiber cable 3 connects the oscillator 1 and a binocular indirect ophthalmoscope 6. It is to be noted that the dichroic mirror 33 has the property of allowing the treatment beam having a wavelength of about 532 nm to pass therethrough and reflecting the aiming beam having a wavelength of about 630 nm.

When pressed down, a footswitch 2 generates a trigger signal for starting irradiation of the treatment beam. A control panel 4 is used to set various irradiation conditions such as output power of the treatment beam. A movement command unit 8 is used for inputting a signal for moving or shifting an irradiation position of the treatment beam (the aiming beam) in two-dimensional, vertical and horizontal directions on the treatment part which is an irradiation target of the treatment beam (the aiming beam). The movement command unit 8 in the present embodiment is a hand-held trackball unit. This movement command unit 8 may be a joystick unit, a mouse unit, etc. which is adapted to input a signal for moving or shifting the irradiation position in the two-dimensional direction. The oscillator 1 also contains a power supply 36 which supplies electric power through a power cable 5 to the binocular indirect ophthalmoscope 6.

The binocular indirect ophthalmoscope 6 includes a fastening band 7 whereby the ophthalmoscope 6 is fixedly mounted on the head of an operator and a scope unit 10 secured to the fastening band 7. A knob 9 is used to change a spot size of the treatment beam (the aiming beam) on the treatment part.

Numeral 50 is an eye of a patient and 51 is an eye of the operator. An ophthalmoscope lens 40 is used to magnify the treatment part of the fundus of the eye 60.

Figure 2:
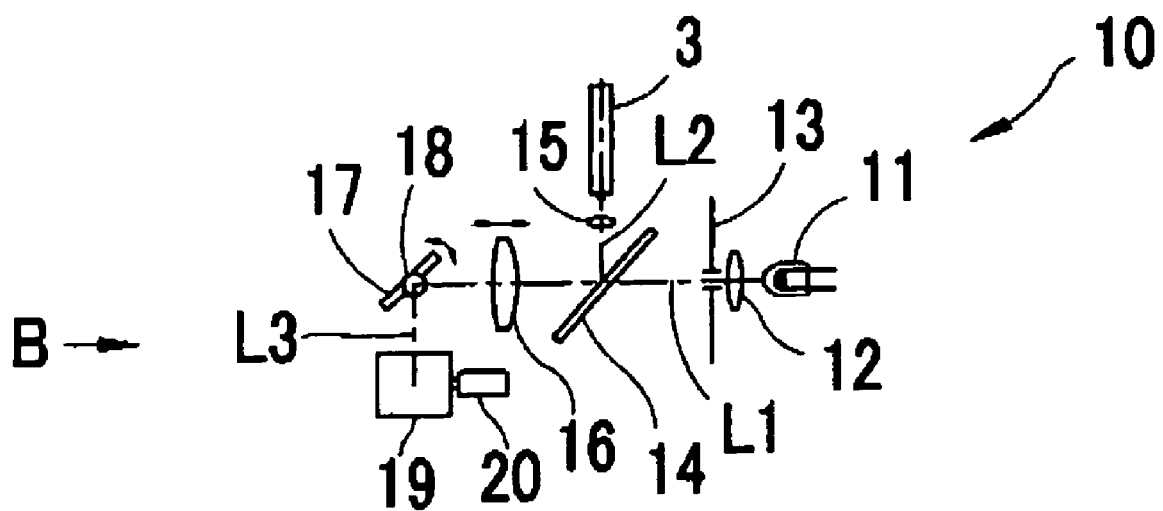
FIG. 2 is a schematic structural view of an optical system in a scope unit of a binocular indirect ophthalmoscope.
Figure 3:
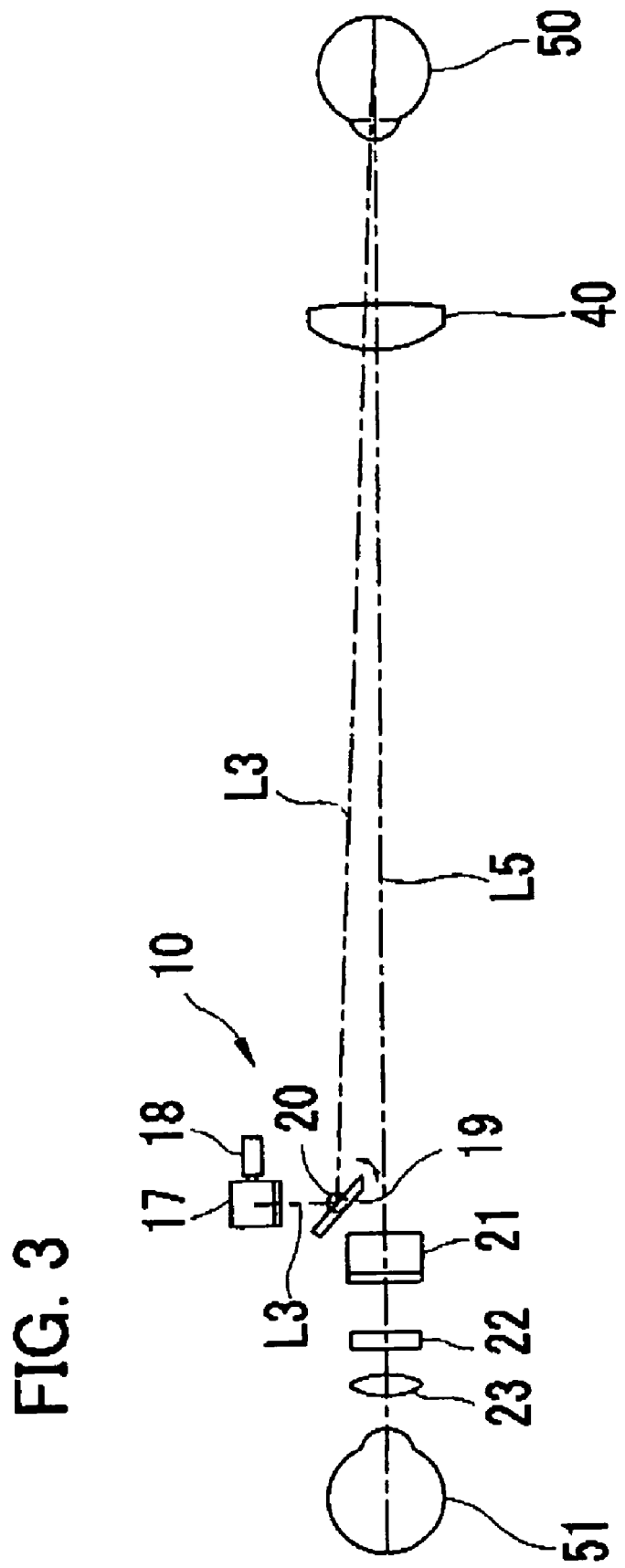
FIG. 3 is a schematic structural view of the optical system in the scope unit of the binocular indirect ophthalmoscope.

FIGS. 2 and 3 are schematic structural views of an optical system in the scope unit 10 of the binocular indirect ophthalmoscope 6. Specifically, FIG. 2 is a view of the optical system disposed in an upper part of the scope unit 10 seen from a direction A in FIG. 1. FIG. 3 is a view of the optical system disposed in a lower part of the scope unit 10 seen from a direction B in FIG. 2.

On an optical axis (path) L1, there are arranged a lamp 11 which is an illumination light source, a condensing lens 12 which condenses illumination light emitted from the lamp 11, and a diaphragm 13.

Both the treatment beam and the aiming beam (hereinafter, "both beams") are emitted from an emission end of the optical fiber cable 3, condensed by the condensing lens 15 disposed on an optical axis (path) L2, and then reflected by a central part of a partially reflecting mirror 14. This mirror 14 is made of a transparent glass and applied, on the central part, with a coating which reflects at least the light having a wavelength of about 532 nm and the light having a wavelength of about 630 nm in order to reflect both beams. A peripheral part of the mirror 14 except the central part is not applied with the coating and therefore allows the illumination light from the lamp 11 to pass therethrough. Thus, the optical axis L1 (the illumination light) and the optical axis L2 (both beams) are brought into coaxial relation. A projection lens 16 projects the coaxially aligned illumination light and both beams onto the eye 50. By rotation of the knob 9, the projection lens 16 is moved in a direction of the optical axis L1 to change a spot size of both beams to be formed on the fundus of the eye 50.

A first galvano mirror 17 and a second galvano mirror 19 serve to vertically and horizontally change the direction of an optical axis (path) L3 of the coaxially aligned illumination light and both beams. In other words, the first galvano mirror 17 is rotated by driving of the first galvanometer 18 to change an inclination angle, thereby changing the direction of the optical axis L3 of the light and beams to be reflected, rightward and leftward. The light and beams reflected by the first galvano mirror 17 are further reflected by a second galvano mirror 19. This mirror 19 is similarly rotated by driving of a second galvanometer 20 to change an inclination angle, thereby changing the direction of the optical axis L3 of the light and beams to be reflected, upward and downward. In this way, the irradiation position of the light and beams can be moved or shifted in the two-dimensional, vertical and horizontal directions. This mechanism may be formed of a single mirror which can be inclined in the two-dimensional direction, instead of using two galvano mirrors as above. The mirror(s) are preferably motor-driven as above, which provides ease of use. Alternatively, it may be manual-operated.

The illumination light and the aiming beam reflected from the eye 50 is magnified by the ophthalmoscope lens 40 and allowed to travel along an optical axis (path) L5 while passing through a right and left splitting mirror 21, a protective filter 22, and an eyepiece lens 23, and enter the eyes 51. Thus, the operator can observe the eye 50. The mirror 21 splits the reflection light and beam from the eye 50 into two beams which come in the right and left eyes 51. The filter 22 blocks the treatment beam reflected from the eye 50 to protect the eyes 51 and also to prevent the entry of dirt into the scope unit 10.

Figure 4:
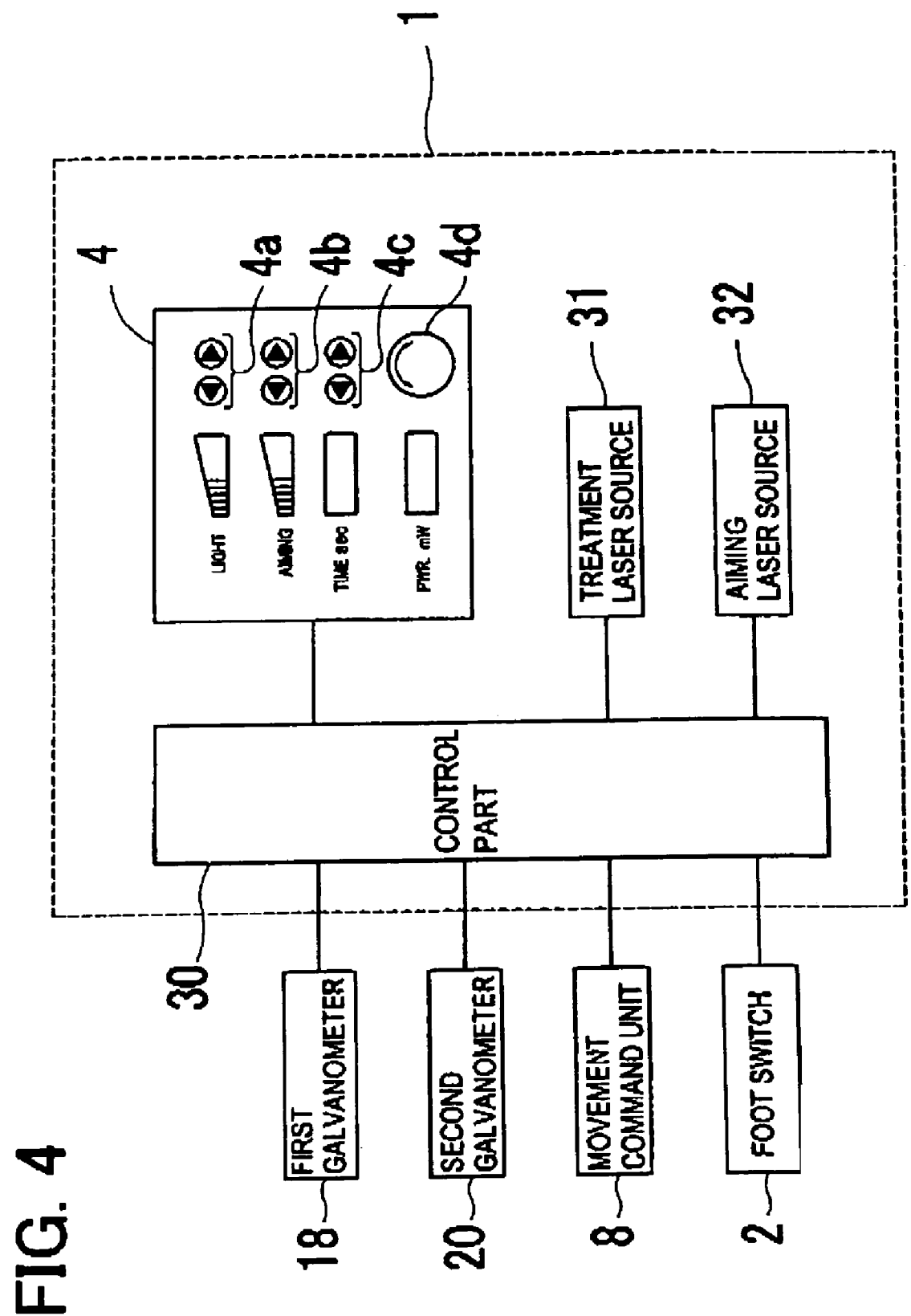
FIG. 4 is a schematic block diagram of a control system in the apparatus.

The operation of the apparatus having the above structure will be explained below, referring to FIG. 4; a schematic block diagram of a control system. The operator mounts the binocular indirect ophthalmoscope 6 on his/her head and adjusts the light quantity of the lamp 11 with the push or touch of a switch 4a on the control panel 4 and the light quantity of the laser source 32 with a switch 4b on the control panel 4. Further, the operator sets an irradiation time (duration) of the treatment beam with a switch 4c on the control panel 4 and output power of the treatment beam with a knob 4b on the control panel 4. Thereafter, he/she holds the ophthalmoscope lens 40 in front of the eye 50 and adjusts a distance between the eye 50 and the binocular indirect ophthalmoscope 6 to a desired treatment distance while observing the eye 50 along the optical axis L5. The operator also makes alignment of the aiming beam from the laser source 32 to the treatment part of the fundus of the eye 50. For aligning the irradiation position of the aiming beam on the fundus to the treatment part, the operator who holds the ophthalmoscope 40 by one hand manipulates the movement command unit 8 by the other hand so that the irradiation position of the aiming beam on the fundus is moved vertically and horizontally for alignment. Specifically, when a trackball of the movement command unit 8 is rotated, a built-in encoder not shown generates a movement command signal for movement in X- and Y-directions to a control part 30. Based on the movement command signal, the control part 30 transmits a driving control signal to the first and second galvanometers 18 and 20 through the cable 5 to rotate individually, thereby directing the irradiation position of the aiming beam to the treatment part desired by the operator.

After completion of alignment of the aiming beam, the operator presses the footswitch 2 to emit the treatment beam. The treatment beam is irradiated to the same position as the irradiation position of the aiming beam through the optical fiber cable 3 and the optical system in the scope unit 10 of the binocular indirect ophthalmoscope. In this way, the treatment part can be treated by photocoagulation.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser treatment apparatus comprising:
    a binocular indirect ophthalmoscope including a fastening band which is to be fixedly mounted on a head of an operator;
    an illumination optical system which is placed in the ophthalmoscope and adapted to illuminate a treatment part of a patient;
    an irradiation optical system which is placed in the ophthalmoscope and adapted to irradiate a treatment laser beam and an aiming beam delivered into the ophthalmoscope to the treatment part;
    at least one drive mirror placed in the irradiation optical system and adapted to shift each irradiation position of the treatment beam and the aiming beam in two-dimensional, vertical and horizontal directions, and to have a reflection surface of which an angle is changeable;
    command means for inputting a shift direction and a shift distance of each irradiation position of the treatment beam and the aiming beam, the command means being arranged to be held by the operator; and
    control means for controlling movements of the at least one drive mirror based on a signal inputted by the command means, the control means being connected to the command means with or without wire.

2. The laser treatment apparatus according to claim 1, wherein the at least one drive mirror shifts an irradiation position of illumination light in the two-dimensional, vertical and horizontal directions.

3. The laser treatment apparatus according to claim 1, wherein the command means includes a trackball and an encoder which detects rotation of the trackball.

* * * * *